(12) United States Patent
Mitchel et al.

(10) Patent No.: US 10,475,531 B2
(45) Date of Patent: *Nov. 12, 2019

(54) METHOD FOR COLLECTING, PROCESSING, AND STORING DISCRETE DATA RECORDS BASED UPON A SINGLE DATA INPUT

(76) Inventors: Jules T. Mitchel, New York, NY (US); Joyce B. Hays, New York, NY (US)

(*) Notice: Subject to any disclaimer, the term of this patent is extended or adjusted under 35 U.S.C. 154(b) by 2 days.

This patent is subject to a terminal disclaimer.

(21) Appl. No.: 13/234,623

(22) Filed: Sep. 16, 2011

(65) Prior Publication Data

US 2012/0022889 A1    Jan. 26, 2012

Related U.S. Application Data

(62) Division of application No. 12/505,206, filed on Jul. 17, 2009, now Pat. No. 8,041,581.

(60) Provisional application No. 61/081,938, filed on Jul. 18, 2008.

(51) Int. Cl.
    *G16H 10/60* (2018.01)
    *G06Q 50/22* (2018.01)
    *G06Q 50/24* (2012.01)
    *G16H 10/20* (2018.01)
    *G06F 19/00* (2018.01)
    *G06F 16/93* (2019.01)

(52) U.S. Cl.
    CPC .......... *G16H 10/60* (2018.01); *G06F 16/93* (2019.01); *G06F 19/00* (2013.01); *G06Q 50/22* (2013.01); *G06Q 50/24* (2013.01); *G16H 10/20* (2018.01)

(58) Field of Classification Search
    CPC .............. G06Q 50/22–24; G16H 50/00–80
    USPC ........................................................ 705/3
    See application file for complete search history.

(56) References Cited

U.S. PATENT DOCUMENTS

| | | | |
|---|---|---|---|
| 6,854,086 B2 * | 2/2005 | Umen et al. ................. | 715/236 |
| 6,925,599 B2 | 8/2005 | Wood | |
| 7,669,114 B2 * | 2/2010 | Wood ........................... | 715/205 |
| 7,752,057 B2 * | 7/2010 | Ikeguchi et al. .............. | 705/2 |
| 2002/0111946 A1 * | 8/2002 | Fallon ............................ | 707/9 |
| 2003/0187688 A1 * | 10/2003 | Fey et al. ....................... | 705/2 |
| 2003/0208378 A1 | 11/2003 | Thangaraj et al. | |
| 2004/0078216 A1 * | 4/2004 | Toto ............................... | 705/2 |
| 2004/0243439 A1 | 5/2004 | Huggard et al. | |

(Continued)

OTHER PUBLICATIONS

Amor, Rudy. "PACS Overview: Past, Present, and Future", Biomedical Instrumentation & Technology; Jul./Aug. 2006; vol. 40, No. 4, p. 281-2.*

*Primary Examiner* — Robert A Sorey
(74) *Attorney, Agent, or Firm* — Kohn & Associates, PLLC

(57) ABSTRACT

A method for the collection, capture, processing, storage and tracking of data for both electronic source health records and for electronic clinical trial purposes by electronically collecting clinical trial data at a clinical trial site, instantly preserving all of the clinical trial data as an electronic source document, archiving the clinical trial data in a trusted data server maintained by a third party, transmitting an acknowledgement upon successful archiving of the clinical trial data, and transmitting the clinical trial data to a clinical trial database only after successful archiving of said clinical trial data. A method for electronically gathering clinical trial data. A method of maintaining discrete data records based upon a single clinical data input.

3 Claims, 1 Drawing Sheet

(56) References Cited

U.S. PATENT DOCUMENTS

| | | |
|---|---|---|
| 2005/0010451 A1 | 1/2005 | Marks et al. |
| 2005/0038673 A1 | 2/2005 | Stookey et al. |
| 2005/0055241 A1 | 3/2005 | Horstmann et al. |
| 2005/0075832 A1* | 4/2005 | Ikeguchi et al. ............... 702/179 |
| 2005/0210026 A1* | 9/2005 | Wood ............................... 707/5 |
| 2006/0259783 A1 | 4/2006 | Work et al. |
| 2006/0155578 A1* | 7/2006 | Eisenberger et al. ............. 705/2 |
| 2006/0248373 A1* | 11/2006 | Warman et al. ................... 714/4 |
| 2007/0005393 A1* | 1/2007 | Cole et al. ........................ 705/2 |
| 2007/0255587 A1* | 11/2007 | Chien et al. ...................... 705/2 |
| 2008/0059241 A1* | 3/2008 | Zahlmann et al. ............... 705/3 |
| 2008/0086337 A1* | 4/2008 | Soon-Shiong .................... 705/3 |
| 2008/0270420 A1 | 4/2008 | Rosenberg |
| 2008/0154640 A1* | 6/2008 | DeMeyer et al. ................ 705/2 |
| 2008/0183497 A1* | 7/2008 | Soon-Shiong .................... 705/2 |
| 2008/0256128 A1 | 10/2008 | Pierce et al. |
| 2011/0161101 A1* | 6/2011 | Ikeguchi et al. .................. 705/2 |

\* cited by examiner

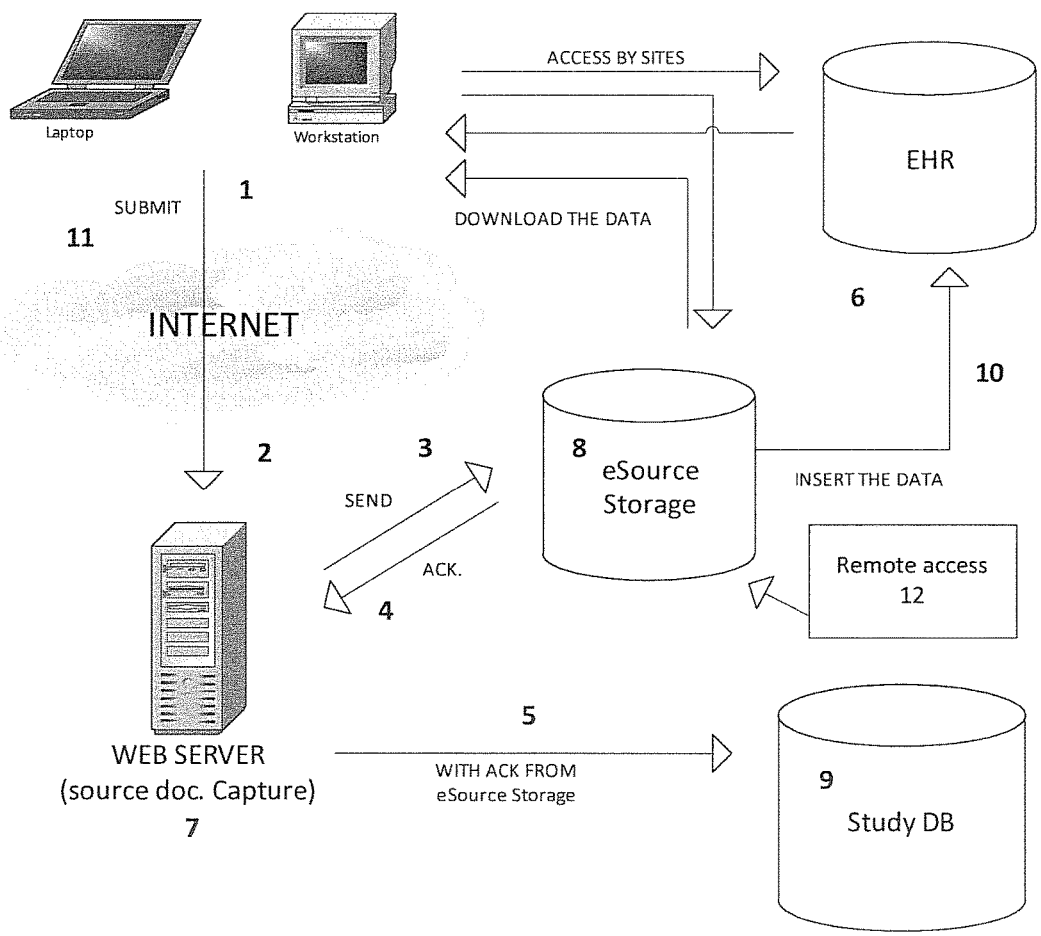

METHOD FOR COLLECTING, PROCESSING, AND STORING DISCRETE DATA RECORDS BASED UPON A SINGLE DATA INPUT

BACKGROUND OF THE INVENTION

Field of the Invention

The present invention generally related to the field of data collection and the processing. Specifically the invention relates to the areas of collecting a single set of data, capturing the data as a source document, processing the data into a variety of formats, and storing the various processed data records in discrete databases.

Description of Related Art

Currently, direct electronic data entry of patient information in clinical trials is rare except for some dedicated Phase 1 units. This is due to the face that current electronic data capture systems, particularly those that are web-based, often fail to comply with the regulations pertaining to the capture and management of source documents as related to clinical trial data. Regulatory agencies, such as the FDA, require that clinical trial data be compiled in a source document, in order to verify the quality and integrity of the trial being conducted.

Electronic data capture tools are currently available which allow the user to collect clinical trial data. However, the clinical research sties still predominantly use paper source documents as the source data when the data are entered into the electronic data capture system. For instance, generally clinical research data are collected and recorded on a paper patient record form, and only later is the form transcribed into an electronic data capture system for clinical trial purposes. As a result, the clinical trial's case report form (CRF) is an abstraction of selected information from the patient record, not the patient record itself. This current industry practice necessitates substantial duplication of effort, and also creates potential for data inaccuracy. Furthermore, the review and processing of these paper records by regulatory agencies (such as the FDA) is a time-consuming and error-prone process.

Thus there exists a significant need for a system capable of both electronic data capture with electronic source document capabilities. A system which provides such a range of functionalities will significantly enhance speed, efficiency and cost savings due to the elimination of transcription errors, source document verification and double-key data entry.

SUMMARY OF THE INVENTION

The present invention provides a system and method for the collection, capture, processing, storage, and tracking of data for both electronic source health records and for electronic clinical trial purposes, based upon a single data collection instance. Upon the collection of data at a clinical trial site, the data are transmitted to a central server where it is captured as an electronic source document(s) in human readable format. The system then transmits the captured electronic source document to a trusted third-party's electronic document repository. Then, the system uses the same captured data to populate the clinical trial's electronic data capture database. The system incorporates security and encryption features to ensure that privacy information requirements are not violated. In the preferred embodiment, the electronic data capture provider for a clinical trial has no control over the server of the trusted third-party vendor, complying with regulatory requirements. Additionally, the collected data can be pushed into a clinical site's electronic health record system or any equivalent system which houses electronic data. Throughout the operation of the system, an audit trail is maintained which records information relating to all data recording, modifying, and accessing events.

BRIEF DESCRIPTION OF THE SEVERAL VIEWS OF THE DRAWINGS

Other advantages of the present invention will be readily appreciated, as the same becomes better understood by reference to the following detailed description when considered in connection with the accompanying drawings wherein:

FIG. 1 represents a conceptual overview diagram of the architecture and sequence of the system and method of the present invention.

DETAILED DESCRIPTION OF THE INVENTION

Generally, the present invention provides a system and method for the collection, capture, processing, storage, and tracking of data for both electronic source health records and for electronic clinical trial purposes, based upon a single data collection instance. Upon the collection of data at a clinical trial site, the data are transmitted to a central server where they are captured as an electronic source document(s) in human readable format. The system then transmits the captured electronic source document to a trusted third-party's electronic document repository. Then, the system uses the same captured data to populate the clinical study's electronic data capture database. The system incorporates security and encryption features to ensure that privacy information requirements are not violated. In the preferred embodiment, the electronic data capture provider for a clinical trial has no control over the server of the trusted third-party vendor, complying with regulatory requirements. Additionally, the collected data can be pushed into a clinical site's electronic health record system or any equivalent system which houses electronic data. Throughout the operation of the system, an audit trail is maintained which records information relating to all data recording, modifying, and accessing events.

FIG. 1 represents a diagram of the system's basic architecture and functionality. Over the course of a clinical trial, data are collected at various remote clinical locations and are inputted to the system using portable laptop computers, handheld devices, or fixed workstations (1). The collected clinical data are then relayed (11) to a central data server (2) via the internet. While in the preferred embodiment the system's user interfaced is deployed via a series of webpages, the system can function similarly using a proprietary software program as well.

Upon receipt of the collected clinical data by the central data server (2), the data are immediately captures (7) in a human-readable file-format (e.g., JPEG, PDF, XML) which serves as the source document. Every submission over the course of the clinical trial, including modifications to existing data, are captured by the central server (2) in a human-readable file format which serves as the source document for the clinical trial. Once the source document has been captured by the central server, the source document is sent (3) to a source data storage server (8). In the preferred embodiment, this server is maintained by an independent third party. The source data server serves as an independent repository of electronic source documents. These documents can be accessed remotely (12) by the clinical study sites, sponsoring pharmaceutical companies as well as regulatory agencies who may need to monitor the quality and integrity of the collected data. Previously, regulatory agencies could only ensure this degree of data integrity by reviewing the collected paper source documents. Upon successful transmission of the source documents to the source data storage server, the source data storage server transmits an acknowledgement (4) back to the central data server, confirming that the source documents have been successfully received.

Upon successful transmission of electronic source document(s) to the source data server, the central server (2) then transmits (5) all collected patient data necessary for clinical trial purposes to a clinical trial database (9). The clinical trial database serves as the central repository of all data necessary to conduct clinical trials.

Additionally, in the preferred embodiment the data collected in the electronic source document server are exported (10) to the electronic health record database (6). This database stores the electronic health records of the individuals participating in the clinical trial, and the data collected at the clinical trial site are added to each individual's health record. In the preferred embodiment, these records will be accessible (based on assigned permissions) to health-care providers at remote clinical sites, as would a paper medical chart.

All data transmissions occurring within the system of the present invention are encrypted to ensure the security of the data. Additionally, in the preferred embodiment, while data which are transmitted to the clinical study database will generally not include a patient's name or identity, the system will assign and/or include other identifying factors such as clinical trial number, site number, and/or patient number. The system of the present invention also incorporates the use of unique user accounts and passwords for each system user. A system administrator assigns each system user a user ID and password, which are used when logging onto the system. Each user is assigned specific permissions by the administrator. The use of unique user ID"s is also critical to the operation of the present invention's audit trail functionality, as described below.

Throughout the operation of the system, all data-related events are logged and stored in an audit trail. The present invention maintains a comprehensive audit trail log and history of all data-related activity and communication occurring within the system, specifically events related to data capture, editing, and access. Doing so allows the system to ensure the integrity of the collected data, by keeping a comprehensive record of all data-related events. This audit trail functionality is particularly significant within the clinical study database, where the integrity of the collected data is of paramount importance. Any modification of data within the clinical study database requires the changing party to provide a reason for the change, and this data is stored together with the record and audit trail within the clinical study database.

The clinical data server of the present invention also allows users to link patient records between different clinical trials. For instance, if a patient is participating in more than one clinical trial, each one of their records within the clinical study database can be linked to one another. This functionality presents an additional dimension to clinical research, which was not previously attainable.

With the implementation of the present invention, significant improvements result in the quality and integrity of data collected both for clinical trial and for electronic source data purposes. Additionally, considerable efficiency and cost savings result. The system and method of the present invention enable users to derive specific types of data records—in the preferred embodiment, electronic source records and electronic clinical study records—from a single central database which is generated based upon a single set of inputs. Configuring the system to comply with all regulatory guidelines ensures the integrity and viability of the data.

While in the preferred embodiment the present invention is directed towards data collection, processing, and storage for electronic health records and clinical trials, the system and method of the present invention can be applied in a broad range of industries and settings. Any setting or industry requiring the maintenance of discrete data records which are derived from a single set of data or a single data collecting event benefits from the increased efficiency and data integrity provided by the present invention.

The invention has been described in an illustrative manner, and it is to be understood that the terminology used is intended to be in the nature of words of description rather than limitation.

Obviously, many modifications and variations of the present invention are possible in light of the above teachings. It is, therefore, to be understood that within the scope of the appended claims, the invention may be practiced otherwise than as specifically described.

What is claimed is:

1. A method of maintaining discrete data records based upon a single clinical data input consisting of the steps of:
   a system user logging into a system for capturing clinical trial data with a unique user ID;
   electronically transmitting clinical trial data and data-related events from a workstation at a clinical location to a central data server;
   instantly capturing the collected clinical trial data and data-related events including existing data and modifications to existing data as an electronic source document in a human-readable file-format in the central data server;
   transmitting, by the central data server, the source document to a source data storage server that is independent of control by the central data server, wherein the central data server is not controlled by the source data storage server;
   securely archiving the source document including existing data and modifications to existing data in the source data storage server on computer readable media;
   transmitting only an acknowledgement from the source data storage server back to the central data server upon successful independent archiving of the source document in the source data storage server;
   transmitting the source document from the central data server to a clinical trial database and preventing deletion of the source document from the source data storage server at any time;
   storing the source document in the clinical trial database;
   remotely accessing the clinical trial data through a remote access interface with the source data storage server; and
   tracking data-related events in the clinical trial database by logging and storing on computer readable media all clinical trial data and clinical trial data-related events in an audit trail by maintaining a comprehensive audit trail log and history of all data-related activity and communications, and providing a reason for any modification of data and storing the modification with the clinical trial data.

2. The method of claim 1, wherein the capturing step further includes generating the electronic source document in the central data server.

3. The method of claim 1, further including the steps of transmitting the clinical trial data from the source data storage server to an electronic health record database, and utilizing the clinical trial data to generate and update an electronic health record in the electronic health record database.

* * * * *